United States Patent
Divekar et al.

(10) Patent No.: US 10,919,871 B2
(45) Date of Patent: Feb. 16, 2021

(54) METHOD OF TREATMENT OF AQUEOUS EFFLUENT

(71) Applicant: BASF SE, Ludwigshafen am Rhein (DE)

(72) Inventors: Sunil Sadashiv Divekar, Pune (IN); Pramod Shankar Kumbhar, Pune (IN); Rahul Vasantrao Bagal, Pune (IN); ShreekantUttam Satav, Pune (IN)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/305,927

(22) PCT Filed: Jun. 1, 2017

(86) PCT No.: PCT/EP2017/063240
§ 371 (c)(1),
(2) Date: Nov. 30, 2018

(87) PCT Pub. No.: WO2017/207679
PCT Pub. Date: Dec. 7, 2017

(65) Prior Publication Data
US 2020/0148656 A1     May 14, 2020

(30) Foreign Application Priority Data

Jun. 2, 2016 (IN) .............................. 201621019001
Jul. 28, 2016 (EP) ..................................... 16181578

(51) Int. Cl.
*C07D 307/50*      (2006.01)
*B01D 3/36*      (2006.01)

(52) U.S. Cl.
CPC ............. *C07D 307/50* (2013.01); *B01D 3/36* (2013.01)

(58) Field of Classification Search
CPC ................................ C07D 307/50; B01D 3/36
USPC .......................................................... 549/490
See application file for complete search history.

(56) References Cited

FOREIGN PATENT DOCUMENTS

| FR | 3006687 B1 | * | 7/2015 | ........... C07D 307/50 |
| WO | 2016025674 A1 | | 2/2016 | |
| WO | 2016113678 A1 | | 7/2016 | |
| WO | 2016113748 A1 | | 7/2016 | |

OTHER PUBLICATIONS

Wikipedia (Isophorone, Nov. 2015, pp. 1-2). (Year: 2007).*
European Search Report for EP Application No. 16181578.2, dated Dec. 12, 2016, 3 pages.
International Search Report for International Application No. PCT/EP2017/063240, dated Aug. 18, 2017, 4 pages.
Written Opinion for International Application No. PCT/EP2017/063240, dated Aug. 18, 2017, 6 pages.

(Continued)

*Primary Examiner* — Taylor V Oh
(74) *Attorney, Agent, or Firm* — Armstrong Teasdale LLP (57) ABSTRACT

A method of treatment of an aqueous effluent stream obtained during production of furfural is disclosed. The aqueous effluent stream containing organic solvents, furfural, and water is subjected to azeotropic distillation to obtain a distillate stream and a treated effluent stream having lower BOD and COD values which can be further reduced by biomethanation.

16 Claims, 1 Drawing Sheet

(56) References Cited

OTHER PUBLICATIONS

Hoydonckx et al., "Furfural and Derivatives", Ullmann's Encyclopedia of Industrial Chemistry, Apr. 15, 2007, Wiley-VCH, Weinheim, Germany (Abstract only).
Curtis and Hatt, "Equilibria in furfural-water systems under increased pressure and the influence of added salts upon the mutual solubilities of furfural and water", Australian Journal of Scientific Research, Jan. 1, 1948, pp. 213-235.
Zeitsch, "Treatment of Furfural Waste Water", the chemistry and technology of furfural and its many by-products, Jan. 1, 2000, pp. 92-97, vol. 13, Elsevier Science B.V., Amsterdam, The Netherlands.

\* cited by examiner

METHOD OF TREATMENT OF AQUEOUS EFFLUENT

CROSS-REFERENCE TO RELATED APPLICATIONS

This application is a U.S. National Phase Application of PCT/EP2017/063240, filed Jun. 1, 2017, which claims the benefit of priority to IN Application No. 201621019001, filed Jun. 2, 2016, and to EP Application No. 16181578.2, filed Jul. 28, 2016, the contents of which are hereby expressly incorporated by reference in their entirety.

FIELD OF INVENTION

The present invention relates to a method of treatment of aqueous effluent. In particular, the presently claimed invention provides a method of treatment of aqueous effluent stream obtained during production of furfural from lignocellulosic feedstocks. Especially, the method comprises a process for simultaneously distillation and recovery of organic solvents from aqueous effluent stream using an azeotropic distillation technique. The said process particularly relates to the treatment of aqueous effluent stream containing organic solvents, for example, MIBK (methyl isobutyl ketone) and ISP (isophorone) as solvents for furfural that form azeotropes with water. Further, said process substantially reduces the COD (Chemical Oxygen Demand) and BOD (Biochemical Oxygen Demand) of said effluent stream.

BACKGROUND OF THE INVENTION

Biomass feedstocks, particularly lignocellulosic biomass eg. such as waste streams produced as low value by-product of various industrial sectors like i.e. agriculture are an alternative for fossil fuels especially regarding global climate change. Lignocellulosic biomass is the most abundantly available renewable feedstock on earth comprising, but not limited to, e.g. waste streams produced as low value by-product of various industrial sectors such as agriculture (e.g. empty fruit bunches, corn stover, straw, bagasse) or forestry (e.g. saw mill, pulp mill residues).

Lignocellulosic biomass [LCM] is typically composed of about 35 to 55% cellulose, 15 to 35% hemicellulose and 15 to 35% lignin. One of the products accessible by processing lignocellulosic biomass is furfural.

Regarding the protection of the global climate, there is a need for optimized methods and processes to produce furfural, for example by decreasing the process steps, avoiding waste and environmental pollution and thereby reducing the present costs and the efforts for future generations.

Industrial aqueous effluent streams, as they arise for example in the production of furfural, may contain varying amounts of organic or inorganic substances. These effluent streams require stringent chemical or biological processing before discharge to natural streams or reuse in industrial or agricultural activities. The compositional complexity of industrial effluents depends on the process wherein they are generated, and is an important aspect for safe and effective treatments of these effluents. Many organic contaminating components of these effluents are common solvents used in chemical syntheses. There are also other organic components of complex nature that are difficult to decompose in nature and are hazardous to different life forms. There have been described many methods of treatment of industrial aqueous effluent or wastewater streams using different types of physical, chemical or biological processes. However, the choice of these processes largely depends on the compositional nature of effluents to be treated for effective use of treatment processes and the positive outcome of the overall methodology used.

In a method of furfural production one or more organic solvents are used during acid catalysed dehydration along with water; and on the completion of said reaction, the reaction mass is separated in an organic phase and an aqueous phase. The furfural formed goes into said organic phase, while the aqueous phase contains soluble reaction waste-products. This aqueous phase or aqueous effluent stream also contains about 2% by weight organic solvents used in soluble form. These organic solvents and reaction waste-products substantially increase the COD and/or BOD of said streams causing problems of effective biomethanation and disposal. An effluent having good amount of organic solvents is not effectively treated with the biological processes due to its tendency to kill or inhibit microbial growth, which is a key requirement for effluent treatment by biological processes.

Thus, there is a need for a method of treatment of aqueous effluent stream obtained during production of furfural such that the COD and BOD values for the treated effluent stream are reduced.

OBJECTS OF THE INVENTION

An object of the presently claimed invention was to provide a method of treatment of aqueous effluent stream generated during the production of furfural, such that the treated effluent stream has low COD and BOD values.

Another object of the presently claimed was to provide a method of treatment of aqueous effluent stream obtained during furfural production, such that the organic solvents in treated effluent stream are present in lower amounts due to which biomethanation takes place more effectively thereby further reducing the COD and BOD values.

It was an object of the invention to provide an efficient method, particularly a continuous process, for the production of furfural from a variety of biomass feedstocks, particularly lignocellulosic biomass waste streams containing xylose. The method should be improved in comparison with the previous processes of the prior art, especially in that not only furfural as product but also the added organic solvents are recovered completely, i.e. the intermediate products where applicable and/or the remainders are essentially free from furfural and added organic solvents.

It was a further object to provide a favourable method, also from an economical point of view, with decreased COD and/or BOD with regard to the remainders.

It was also an object to provide a method in which as many as possible amounts of the product (furfural) and of organic solvents are recovered.

SUMMARY OF THE INVENTION

Surprisingly, it has been found that when aqueous effluent stream containing at least one organic solvent, furfural and water is subjected to azeotropic distillation, the COD of the aqueous effluent stream is reduced by 30% to 45% of the original COD value of the aqueous effluent stream and the BOD of the aqueous effluent stream is reduced by 20% to 40% of the original BOD value of the aqueous effluent stream.

Further, when the treated effluent stream is subjected to biomethanation step, the COD is reduced by 45% to 85% of the COD value of treated effluent stream and BOD is reduced by 35% to 80% of the BOD value of treated effluent stream.

Thus, for the aqueous effluent stream, the overall COD reduction is 70% to 90% of the original COD value of the aqueous effluent stream and the overall BOD reduction is 55% to 85% of the original BOD value of the aqueous effluent stream.

Furthermore, the distillate stream comprises the top organic layer and the lower aqueous layer, components of which can be recycled into the main organic and aqueous phase, respectively, thus increasing the overall efficiency of the method of production of furfural.

The object of the instant invention has been solved by the matter outlined in present claim 1. The dependant claims as well as the description and examples show further embodiments of the present invention.

The method of the invention herein disclosed provides a new method of recovery of organic solvents and furfural that are able to form azeotropes with water.

In the following, specific embodiments of the present invention are described:

1. In an embodiment, the presently claimed invention is directed to a method of treatment of an aqueous effluent stream by subjecting the aqueous effluent stream containing at least one organic solvent, furfural and water to azeotropic distillation to obtain a distillate stream and a treated effluent stream.

2. The method according to embodiment 1, wherein the aqueous effluent stream is obtained by:
   i) pre-treating the lignocellulosic biomass with mineral or organic acids to obtain soluble C5 sugar fraction containing xylose;
   ii) adjusting the pH of the soluble C5 sugar fraction obtained in step i);
   iii) treating the pH adjusted soluble C5 sugar fraction with at least one organic solvent to obtain a feed stream with an aqueous phase and an organic phase;
   iv) subjecting the feed stream obtained in step iii) to a temperature in the range of ≥160° C. to ≤220° C. for a period in the range of ≥10 minutes to ≤2 hours, to obtain a reaction mass comprising furfural;
   v) filtering the reaction mass of step iv) to obtain the liquid fraction; and
   vi) subjecting the liquid fraction obtained in step v) to phase separation to obtain an organic phase comprising furfural and the at least one organic solvent, and an aqueous effluent stream comprising the at least one organic solvent, furfural and water.

3. The method according to embodiment 1 or 2, wherein the at least one organic solvent is selected from the group consisting of cyclic ketones, dialkyl ketones and benzene derivatives.

4. The method according to embodiment 3, wherein the cyclic ketones are selected from the group consisting of isophorone, cyclohexanone and cyclopentanone.

5. The method according to embodiment 3, wherein the dialkyl ketones are selected from the group consisting of methyl isobutyl ketone, methyl ethyl ketone, dipropyl ketone, ethyl butyl ketone, diisobutyl ketone, methyl amyl ketone, methyl propyl ketone and 5-methyl-2-hexanone.

6. The method according to embodiment 3, wherein the benzene derivatives are selected from the group consisting of toluene, xylene, sec-butyl phenol, diphenyl oxide and methyl phenyl ketone.

7. The method according to one or more of embodiments 1 to 6, wherein the at least one organic solvent is at least two organic solvents.

8. The method according to embodiment 7, wherein the at least two organic solvents are selected from the group consisting of cyclic ketones, dialkyl ketones and benzene derivatives.

9. The method according to embodiment 7, wherein the at least two organic solvents are selected from the group consisting of isophorone, cyclohexanone, cyclopentanone, methyl isobutyl ketone, methyl ethyl ketone, dipropyl ketone, ethyl butyl ketone, diisobutyl ketone, methyl amyl ketone, methyl propyl ketone, 5-methyl-2-hexanone, toluene, xylene, sec-butyl phenol, diphenyl oxide and methyl phenyl ketone.

10. The method according to embodiment 7 or 8, wherein the at least two organic solvents are methyl isobutyl ketone and isophorone.

11. The method according to embodiment 10, wherein methyl isobutyl ketone and isophorone are present in a ratio in the range of 95:5 and 60:40.

12. The method according to embodiment 10 or 11, wherein methyl isobutyl ketone and isophorone are present in a ratio of 80:20.

13. The method according to embodiment 2, wherein the ratio of the aqueous phase to the organic phase in step iii) is in the range of 1:0.5 to 1:3.5.

14. The method according to embodiment 2, wherein the ratio of the aqueous phase to the organic phase in step iii) is in the range of 1:0.75 to 1:3.2.

15. The method according to embodiment 2, wherein the mineral or organic acids in step i) are selected from the group consisting of sulphuric acid, phosphoric acid, oxalic acid or mixtures thereof.

16. The method according to embodiment 2, wherein the pH of soluble C5 sugar fraction in step i) is adjusted in the range of ≥1 to ≤2.

17. The method according to embodiment 2, wherein in step iv) the temperature is in the range of ≥170° C. to ≤210° C.

18. The method according to embodiment 2, wherein in step iv) the temperature is in the range of ≥180° C. to ≤200° C.

19. The method according to embodiment 2, wherein step iv) is carried out in a reactor vessel.

20. The method according to embodiment 19, wherein the reactor vessel is selected from the group consisting of autoclave vessel, stirred-tank, mechanically agitated stirred-tank type or continuous type, batch type closed stirred-tank reactor, plug-flow reactor, continuous stirred-tank reactor and continuous plug-flow reactor.

21. The method according to embodiment 2, wherein in step v) the reaction mass is filtered using a solid-liquid separator, decanter, or a decanter centrifuge.

22. The method according to one or more of embodiments 2 to 10, wherein the organic phase of step vi) comprises methyl isobutyl ketone in the range of ≥55 wt.-% to ≤70 wt.-%, isophorone in the range of ≥10 wt.-% to ≤wt.-20% and furfural in the range of ≥5 wt.-% to ≤wt.-10%.

23. The method according to embodiment 1 or 2, wherein the aqueous effluent stream has a pH in the range of ≥1 to ≤2.

24. The method according to embodiment 1, wherein the azeotropic distillation is carried out at a temperature in the range of ≥80° C. to ≤100° C.

25. The method according to embodiment 1, wherein the azeotropic distillation is carried out at a temperature in the range of ≥90° C. to ≤98° C.

26. The method according to embodiment 1, wherein the azeotropic distillation is carried out at a temperature in the range of ≥94° C. to ≤96° C.

27. The method according to embodiment 1, wherein the azeotropic distillation is carried out at a pressure in the range of ≥650 mmHg to ≤760 mmHg.

28. The method according to embodiment 1 or 2, wherein the concentration of the at least one organic solvent in the aqueous effluent stream is in the range of ≥0.05 wt.-% to ≤2 wt.-%.

29. The method according to embodiment 1 or 2, wherein the concentration of methyl isobutyl ketone in the aqueous effluent stream is in the range of ≥0.15 wt.-% to ≤0.85 wt.-%.

30. The method according to embodiment 1 or 2, wherein the concentration of isophorone in the aqueous effluent stream is in the range of ≥0.05 wt.-% to ≤0.45 wt.-%.

31. The method according to embodiment 1 or 2, wherein the concentration of furfural in the aqueous effluent stream is in the range of ≥0.1 wt.-% to ≤0.5 wt.-%.

32. The method according to embodiment 1 or 2, wherein the concentration of water in the aqueous effluent stream is in the range of ≥50 wt.-% to ≤99 wt.-%.

33. The method according to embodiment 1 or 2, wherein methyl isobutyl ketone, isophorone, furfural and water in the aqueous effluent stream are in the ratio in the range of 1.5:1:1:200 and 3:1:2:2000.

34. The method according to embodiment 1, wherein the treated effluent stream is essentially free from methyl-isobutyl ketone, isophorone, and furfural.

35. The method according to embodiment 1, wherein the distillate stream is subjected to a phase separation step to obtain a top organic layer and a lower aqueous layer.

36. The method according to embodiment 35, wherein the top organic layer is combined with the organic phase of step vi).

37. The method according to embodiment 35, wherein the lower aqueous layer is combined with the aqueous effluent stream of step vi).

38. The method according to one or more of embodiments 1 to 37, wherein after the azeotropic distillation the COD of the aqueous effluent stream is reduced by 30% to 45% of the original COD value of the aqueous effluent stream; and the BOD of the aqueous effluent stream is reduced by 20% to 40% of the original BOD value of the aqueous effluent stream.

39. The method according to embodiment 1 or 2 further comprising the step of biomethanation of the treated effluent stream subsequent to the azeotropic distillation.

40. The method according to one or more of embodiments 1 to 39, wherein when the treated effluent stream is subjected to biomethanation step, the COD is reduced by 48% to 85% of the COD value of treated effluent stream and BOD is reduced by 35% to 80% of the BOD value of treated effluent stream.

41. The method according to one or more of embodiments 1 to 40, wherein for the aqueous effluent stream the overall COD reduction is 70% to 90% of the original COD value of the aqueous effluent stream and the overall BOD reduction is 55% to 85% of the original BOD value of the aqueous effluent stream.

42. A method for producing furfural using MIBK (methyl-isobutyl-ketone) and ISP (isophorone) as solvents for furfural, wherein MIBK, ISP and furfural are removed from an aqueous effluent in one distillation step.

Definition of Terms

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

The term lignocellulosic biomass as used herein shall be understood to comprise waste streams produced as low value by-product of various industrial sectors such as agriculture (e.g. empty fruit bunches, corn stover, straw, bagasse) or forestry (e.g. saw mill, pulp mill residues) as well as virgin material (e.g. wood, energy cane).

The term C5 sugars fraction stand for a hydrolysate stream containing C5 and C6 sugar oligomers (pentosans and glucosans, respectively) and preferably monomers (pentoses and hexoses), more preferably predominantly pentoses including but not limited to arabinose, ribose, ribulose, xylose, xylulose, and their etherified or esterified derivatives; monomeric pure xylose is most preferred.

The term feed stream refers to an acid pre-treated lignocellulosic biomass from which the insoluble fraction has been removed and the soluble aqueous C5 sugar fraction comprising xylose and acids has been mixed with organic solvents.

Reaction mass comprising furfural is obtained when the feed stream which is subjected to a high temperature in the range of ≥160° C. to ≤220° C. for a period in the range of ≥10 minutes to ≤2 hours in a high-pressure reactor.

The term azeotropic distillation generally refers to the specific technique of adding another component to generate a new, lower-boiling azeotrope that is heterogeneous (e.g. producing two, immiscible liquid phases).

The term quaternary azeotrope refers to an azeotrope mixture having four components.

The term aqueous effluent stream refers to the aqueous phase obtained upon phase separation of the liquid fraction of the reaction mass, after removing the organic phase.

The term distillate stream refers to the stream obtained after azeotropic distillation of aqueous effluent stream. The distillate stream comprises a top organic layer and a lower aqueous layer.

The term bottom refers to the treated effluent stream. The treated effluent stream is essentially free from MIBK, ISP and/or furfural. The treated effluent stream is subjected to biomethanation to further reduce the COD and BOD values.

The term "essentially free from" in respect of the treated effluent stream, means that merely traces of the components MIBK, ISP and/or furfural might be present in the mixture, especially that the analytical methods for qualitative and/or quantitative detection of the aforementioned compounds result in concentrations of less than 0.1 wt.-%. For example, the concentration of MIBK is in the range of ≥0 wt.-% to ≤0.05 wt.-%, the concentration of ISP is in the range of ≥0.01 wt.-% to ≤0.05 wt.-% the concentration of furfural is in the range of ≥0.02 wt.-% to ≤0.08 wt.-%.

Biomethanation refers to a process by which organic material is microbiologically converted under anaerobic conditions to biogas. Microorganisms degrade organic matter via cascades of biochemical conversions to methane and carbon dioxide.

Chemical oxygen demand (COD) is an indicative measure of the amount of oxygen that can be consumed by reactions in a measured solution. It is commonly expressed in mass of oxygen consumed over volume of solution. A COD test can be used to easily quantify the amount of organics in water. COD is useful in terms of water quality by providing a means to determine the effect an effluent will have on the receiving water body.

Biological oxygen demand (BOD) refers to the amount of dissolved oxygen needed by aerobic biological organisms to break down organic material present in a given water sample at certain temperature over a specific time period. The BOD value is most commonly expressed in milligrams of oxygen consumed per litre of sample during 5 days of incubation at 20° C. and is often used as an indicator of organic pollution of water.

It must also be noted that, as used in the specification and the appended claims, the singular forms "a", "an" and "the" include plural referents unless otherwise specified.

As used herein, the term "about" when combined with a value refers to plus and minus 10% of the reference value unless otherwise specified. For example, a temperature of about 50° C. refers to a temperature of 50° C.±5° C., etc.

Any indications of quantity given in the instant invention are to be considered as indications of quantity by weight, if not specified otherwise.

Reactions or process steps of the present invention are carried out at atmospheric pressure of 760 mmHg. A person skilled in the art is aware of the fact that boiling point, distillation temperature etc. depends on the atmospheric pressure or the pressure of the system in which the steps are carried out. Therefore, a change in the pressure causes changes in boiling point, distillation temperature etc. Nevertheless, the person skilled in the art determines these changes by simple methods like temperature measurement or by means of tables from the prior art.

In the instant invention, the term "and/or" includes any and all combinations of one or more of the associated listed items.

DETAILED DESCRIPTION

Figure 1:
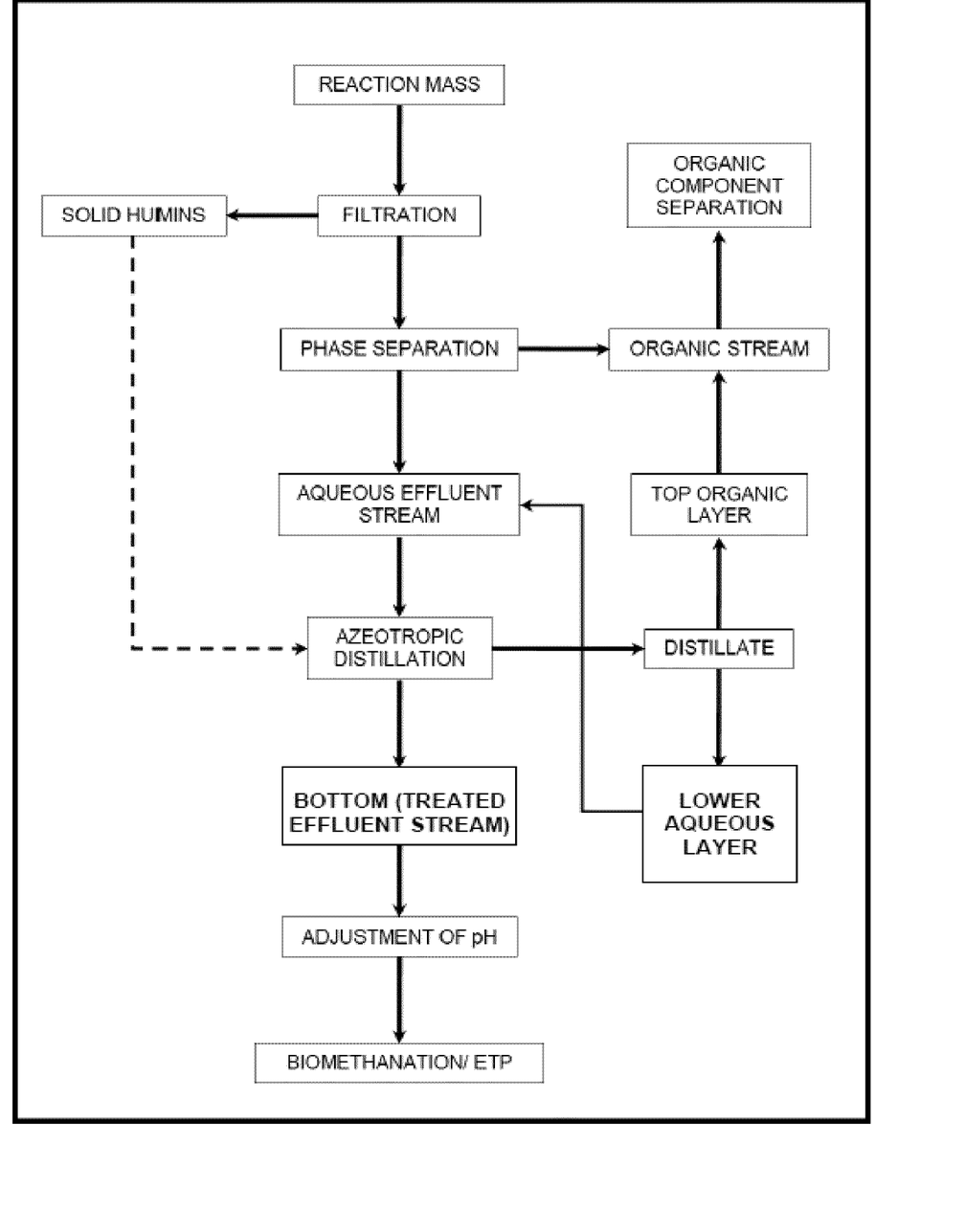
FIG. 1 depicts a process flow diagram of a preferred embodiment for the recovery of organic solvents from industrial effluents ie. aqueous effluent stream. Different elements of the process are identified and directional movement of different streams during the process is shown to describe the features of present invention.

The presently claimed invention provides a method of treatment of aqueous effluent stream generated during the production of furfural, using an azeotropic distillation technique.

In one embodiment of the invention, in a method for the preparation of furfural from lignocellulosic biomass e.g. such as LCM waste streams, after pre-treatment the C5 sugar fraction comprising xylose, of the acid treated lignocellulosic biomass is separated and subjected to furfural preparation by a thermo-chemical process in which organic solvents are used in aqueous reaction mixture. Upon completion of the reaction, the reaction mass is separated in an organic phase and an aqueous phase. The organic phase contains most of furfural and the organic solvents used like MIBK (methyl isobutyl ketone), isophorone (ISP), etc. The aqueous phase contains soluble humins and small amounts of the organic components not more than about 2% by weight coming from the solvents used along with the product and by-products of the thermo-chemical treatment. The said aqueous phase forms the aqueous effluent stream, which has high COD and BOD due to large amounts of the organic substances in it.

The aqueous effluent stream contains at least one organic solvent, furfural and water.

In one embodiment of the invention the at least one solvent selected from the group consisting of cyclic ketones, dialkyl ketones and benzene derivatives.

In another embodiment of the invention, the cyclic ketones are selected from the group consisting of isophorone, cyclohexanone and cyclopentanone.

In yet another embodiment of the invention, the dialkyl ketones are selected from the group consisting of methyl isobutyl ketone, methyl ethyl ketone, dipropyl ketone, ethyl butyl ketone, diisobutyl ketone, methyl amyl ketone, methyl propyl ketone and 5-methyl-2-hexanone.

In another embodiment of the invention, the benzene derivatives are selected from the group consisting of toluene, xylene, sec-butyl phenol, diphenyl oxide and methyl phenyl ketone.

In an embodiment of the invention, the at least one organic solvent is at least two organic solvents.

In another embodiment of the invention, the at least two organic solvents are selected from the group consisting of cyclic ketones, dialkyl ketones and benzene derivatives.

In yet another embodiment of the invention, the at least two organic solvents are selected from the group consisting of isophorone, cyclohexanone, cyclopentanone, methyl isobutyl ketone, methyl ethyl ketone, dipropyl ketone, ethyl butyl ketone, diisobutyl ketone, methyl amyl ketone, methyl propyl ketone, 5-methyl-2-hexanone, toluene, xylene, sec-butyl phenol, diphenyl oxide and methyl phenyl ketone.

In a preferred embodiment of the invention, the at least two organic solvents are methyl isobutyl ketone and isophorone.

The method of the invention disclosed herein is essentially directed to the treatment (purification) of the aqueous effluent stream.

In one embodiment, the invention is directed to a method for producing furfural using MIBK (methyl isobutyl ketone) and ISP (isophorone) as solvents for furfural, wherein MIBK, ISP and furfural are removed from an aqueous effluent in one distillation step.

Due to this one distillation step the added organic solvents such as MIBK and ISP for furfural, as well as the product furfural are removed so that the aqueous effluent is essentially free from MIBK, ISP and/or furfural.

In another embodiment of the invention, the one distillation step is an azeotropic distillation.

The distillate is used for the separation of said organic solvents in pure form for reuse and also to reduce the COD and BOD of the effluents formed in the process of the invention.

In a further embodiment, the one distillation step is a distillation of a quaternary azeotrope.

In another embodiment, the one distillation step is a heterogeneous azeotropic distillation. This allows a very simple separation of the top organic phase of the distillate from the bottom aqueous phase, for example by decantation or using a separating funnel and in one alternative without a distillation step.

In a further embodiment MIBK, ISP, furfural and water are removed in one distillation step as a quaternary azeotrope with a boiling point of about 88° C. at atmospheric pressure.

The one distillation step is carried out in one embodiment at a temperature of 80° C. to 100° C., preferably at 90° C. to 98° C., especially 94° C. to 96° C. at atmospheric pressure.

In another embodiment, the concentration of MIBK is from 0.15 wt.-% to 0.85 wt.-%, the concentration of ISP is 0.05 wt.-% to 0.45 wt.-%, the concentration of furfural is from 0.1 wt.-% to 0.5 wt.-%, the amount of water from 95 wt.-% to 98 wt.-% in the aqueous effluent. The aqueous effluent comprises at least 50 wt.-%, 60 wt.-% preferably 70 wt.-%, 80 wt.-%, more preferably 90 wt.-%, 91 wt.-%, 92 wt.-%, 93 wt.-%, 94 wt.-%, especially at least 95 wt.-% of water.

According to one embodiment the aqueous effluent is the result of a phase separation of a liquid fraction in an organic phase and the aqueous effluent.

The ratio of MIBK:ISP:furfural:water in the aqueous effluent is between 1.5:1:1:200 and 3:1:2:2000.

A further subject matter is a quaternary, preferably heterogeneous azeotrope of MIBK, ISP, furfural and water, wherein the concentration of MIBK is from about 55 to 65%, the concentration of ISP is from about 20 wt.-% to 25 wt.-%, the concentration of furfural is from about 12 wt.-% to 18 wt.-%; whereby the total amount including the concentration of water is 100%. Additionally, water has to be present for the formation of the quaternary azeotrope, at least in a concentration of 0.1% wt.-.

In one embodiment, the method of the invention comprises said one distillation step wherein the concentration of MIBK is from about 55 wt.-% to 65 wt.-%, the concentration of ISP is from about 20 wt.-% to 25 wt.-%, the concentration of furfural is from about 12 wt.-% to 18 wt.-% in the quaternary azeotrope; whereby the total amount including the concentration of water is 100 wt.-%. Additionally, water has to be present for the formation of the quaternary azeotrope, at least in a concentration of 0.1 wt.-%.

In an embodiment, the quaternary azeotrope has a boiling point in the range of ≥70° C. to ≤90° C. at atmospheric pressure.

According to one embodiment the treated aqueous effluent after the one distillation step is essentially free of MIBK, ISP and/or furfural.

In another embodiment, the method according to the invention comprises at least one of the following steps before the one distillation step:

Step 1: Providing a C5 sugar fraction comprising xylose obtained from an acid pre-treated lignocellulosic biomass eg. such as LCM waste streams; optionally removing an insoluble fraction from the acid pre-treated lignocellulosic biomass to obtain soluble C5 sugar fraction containing xylose; adjusting the pH of the soluble C5 sugar fraction; and mixing with organic solvents MIBK and ISP;

Step 2: Converting xylose in furfural by heating the mixture;

Step 3: Separating the solid fraction; and/or

Step 4: Separating the organic phase from the liquid fraction of step 3 and isolating furfural.

In another embodiment of the invention, the said process comprises seven steps:
step 1] preparation of feed stream;
step 2] preparation of reaction mass;
step 3] filtration of reaction mass;
step 4] phase separation;
step 5] azeotropic distillation;
step 6] biomethanation and
step 7] treatment of distillate stream.

Herein each step may comprise one or more elements to be performed specifically or optionally as required for the recovery of organic solvents and for the safely and eco-friendly treatment of said aqueous effluent stream. A person skilled in the art may appreciate different variations and/or combinations of these elements that may be used to perform the objects of the invention disclosed herein.

Step 1: Preparation of Feed Stream

In one embodiment of the invention, the lignocellulosic biomass e.g. such as LCM waste streams is pre-treated with mineral or organic acids and insoluble fraction is removed. The pre-treatment can be carried out with mineral or organic acids, preferably selected from the group consisting of $H_2SO_4$, $H_3PO_4$, oxalic acid and mixtures thereof.

The remaining soluble fraction comprises xylose and the acids in watery stream. The pH of said soluble fraction is adjusted with a base to be between 1 and 2 and is mixed with a mixture of solvents forming a feed stream. The solvents used are MIBK with isophorone, in a ratio MIBK:ISP of between 95:5 and 60:40, preferably 80:20. Additionally, other organic solvents like toluene, diphenyloxide, sec-butylphenol, cyclohexanone, cyclopentanone, methyl isobutyl ketone, methyl ethyl ketone, dipropyl ketone, ethyl butyl ketone, diisobutyl ketone, methyl amyl ketone, methyl propyl ketone, 5-methyl-2-hexanone, xylene, methyl phenyl ketone or combination thereof may also be used.

In one embodiment, the ratio of aqueous phase to organic phase in this step is adjusted to be from 1:0.5 to 1:3.5, preferably 1:0.75 to 1:3.2 by weight.

In one embodiment, no additional salt (or salts) or aqueous solution thereof are added during the process according to the invention. In one alternative no additional salt (or salts) or aqueous solution thereof are added in acid pre-treatment of the process according to the invention. The streams respectively the solutions of the invention, especially in step 1, may comprise salt, especially sulphate and/or phosphate salts, which are formed due to chemical reaction in situ, but no active addition of salt(s) takes place.

A salt is defined, according to the present invention, as a compound resulting from a chemical reaction between an acid and a base, in which the acid's hydrogen atoms are replaced by cations of the base. Cations are metal cations or quaternary ammonium cations.

Step 2: Preparation of Reaction Mass

In one alternative a fluid comprising or consisting of the soluble fraction of the acid treatment of lignocellulosic biomass C5 sugar fraction comprising xylose and the acids is discharged into a reactor vessel.

In another embodiment of the invention, said feed stream is subjected to a high temperature of between 160° C. to 220° C., preferably between 170° C. to 210° C., more preferably between 180° C. to 200° C., for between 10 minutes to 2 hours in a high-pressure reactor leading to the formation of a reaction mass. The reactor used in this step may be CSTR batch type, mechanically agitated stirred type or continuous type wherein the residence time is between 10 minutes to 2 hours at a high temperature of between 160° C. to 220° C. At these conditions xylose present in the feed stream is converted to furfural due to the acidic dehydration.

In one embodiment of the present invention, said reactor vessel is an autoclave vessel. In another embodiment of the present invention, said reactor is a batch type closed stirred tank reactor. In yet another embodiment of the present invention, said reactor is a plug-flow reactor. In yet another, preferred embodiment of the present invention, said reactor is a continuous stirred-tank reactor or a continuous plug-flow reactor.

In alternatives, the reactor used may be stirred-tank type, mechanically agitated stirred type or continuous type.

After the conversion, in one alternative of more than 90% of xylose the whole of the reaction mass is subjected the next step of processing.

Step 3: Filtration of Reaction Mass

In one embodiment of the invention, said reaction mass of Step 2 is cooled to room temperature and solid fraction is in one embodiment of the invention separated from liquid fraction using a solid-liquid separator, for example by filtration or using a decanter or decanter centrifuge. This leads to the removal of insoluble humins from said reaction mass.

Step 4: Phase Separation

In another embodiment of the invention, said liquid fraction is subjected to a phase separation step into an aqueous phase and a main organic phase. Then said main organic phase is removed from an aqueous phase [a.k.a. (also known as) aqueous effluent stream] and subjected to pH adjustment to 7 by $NaHCO_3$. The said main organic phase comprises in one embodiment 64 wt.-% of MIBK, 16 wt.-% of isophorone and 8 wt.-% of furfural all by weight. It is next subjected to a normal distillation to recover pure organic components.

While said aqueous effluent stream is subjected to one distillation step, in one embodiment an azeotropic distillation (step) operation.

Step 5: Azeotropic Distillation

In one embodiment of the invention, said aqueous effluent (stream) comprising at least two organic solvents and furfural along with unreacted sugars, soluble humins and soluble salts, is subjected to an azeotropic distillation operation. The pH of the effluent is between 1.8 to 2 with a dark colouration. The COD and BOD of said aqueous effluent stream is also very high.

To reduce the COD and BOD and to recover the organic components, said stream is subjected to azeotropic distillation at 80° C. to 100° C., preferably at 90° C. to 98° C., especially 94° C. to 96° C. at atmospheric pressure. The said azeotropic distillation gives a distillate stream and a bottom stream—also called a treated effluent stream—with up to 40% reduction of COD and up to 35% BOD reduction over the input stream ie. aqueous effluent stream. This step improves the quality of said treated effluent stream in terms of reduction of COD and BOD, which is further subjected for biomethanation.

Optionally, after filtration of reaction mass, the separated solid humins [from Step 3] containing traces of the solvents and the product is mixed with said aqueous effluent stream to recover extra organic components from it.

Step 6: Biomethanation

In one embodiment of the invention, said treated effluent stream [now containing fewer amounts of organic components] is subjected to a step of anaerobic biomethanation after increasing its pH to 6 using magnesium oxide. The pH of final stream after biomethanation is 7.7 and this treatment shows at least 45% reduction in COD and at least 35% reduction in BOD over the input stream ie. treated effluent stream values. The overall reduction in the COD in the process of the invention is up to 85% and overall reduction in the BOD is up to 80% of the original values ie. values for aqueous effluent stream.

Step 7: Treatment of Distillate Stream

In yet another embodiment of the invention, said distillate stream comprises two phases, a top organic layer and a lower aqueous layer.

The said top organic layer after separation is mixed with main organic phase for recovery. While said lower aqueous layer having finite amount of organic components is mixed with said aqueous effluent stream and treated to increase the overall efficiency of the process.

The various embodiments of the instant invention, including those of the dependent claims, can be combined with each other in any desired manner. The invention will now be explained by way of the following non-limiting examples.

In one embodiment, the process for producing furfural is analogous to the one disclosed in the application PCT/IB2016/050138, which is incorporated by reference, and comprises additionally the method of treatment of aqueous effluent stream obtained during production of furfural according to the present invention.

In the following, specific embodiments of the present invention are described:

1. A method for producing furfural using MIBK (methyl-isobutyl-ketone) and ISP (isophorone) as solvents for furfural, wherein MIBK, ISP and furfural are removed from an aqueous effluent in one distillation step.
2. The method according to embodiment 1, wherein the one distillation step is an azeotropic distillation.
3. The method according to any of the preceding embodiments, wherein the one distillation step is a distillation of a quaternary azeotrope.
4. The method according to any of the preceding embodiments, wherein the one distillation step is a heterogeneous azeotropic distillation.
5. The method of any of the preceding embodiments, wherein MIBK, ISP, furfural and water are removed in one distillation step as a quaternary azeotrope with a boiling point of 88° C. at atmospheric pressure.
6. The method according to any of the preceding embodiments, wherein the one distillation step is carried out at a temperature of 80° C. to 100° C., preferably at 90° C. to 98° C., especially 94° C. to 96° C. at atmospheric pressure.
7. The method according to any of the preceding embodiments, wherein the concentration of MIBK is from 0.15% to 0.85%, the concentration of ISP is 0.05% to 0.45%, the concentration of furfural is from 0.1% to 0.5%, in the aqueous effluent.
8. The method according to any of the preceding embodiments, wherein the concentration of MIBK is from about 55% to 65%, the concentration of ISP is from about 20% to 25%, the concentration of furfural is from about 12% to 18%, in the quaternary azeotrope.
9. A method according to any of the preceding embodiments, wherein the aqueous effluent is the result of a phase separation of a liquid fraction in an organic phase and the aqueous effluent.
10. The method according to any of the preceding embodiments, wherein the treated aqueous effluent after the one distillation step is essentially free of MIBK, ISP and/or furfural.
11. A method according to any of the preceding embodiments, comprising at least one of the following steps before the one distillation step:
Step 1: Providing C5 sugar fraction comprising xylose obtained from an acid pre-treated lignocellulosic biomass and mixing with organic solvents MIBK and ISP,
Step 2: Converting xylose in furfural by heating the mixture,
Step 3: Separating the solid fraction, Step 4: Separating the organic phase from the liquid fraction of step 3 and isolating furfural.

12. A method according to embodiment 11, wherein in step 1 an insoluble fraction is removed from the acid pre-treated lignocellulosic biomass.

13. A method according to embodiments 1, 11 and/or 12, wherein the pH of the respective mixture is adjusted in at least one step.

14. A method according to any of the preceding embodiments, wherein the distillate of the one distillation step of claim 1 is separated in an organic phase and an aqueous phase.

15. A method according to any of the proceeding embodiments, wherein the treated effluent stream is subjected to an anaerobic biomethanation.

Advantages

The presently claimed method of treatment of aqueous effluent stream generated during the production of furfural offers one or more of the following advantages:

1. The overall COD and BOD values of the aqueous effluent stream are reduced by 70% to 85% of the original COD value of the aqueous effluent stream; and 55% to 80% of the original BOD value of the aqueous effluent stream, respectively.

2. The method of treatment of aqueous effluent stream ensures that the organic solvents in treated effluent stream are in lower amounts such that biomethanation takes place more effectively thereby further reducing the COD and BOD values.

3. The top organic layer and the lower aqueous layer of the distillate stream is combined with the main organic phase and the aqueous phase, respectively, thereby increasing the overall efficiency of the method of production of furfural.

Examples provided below give wider utility of the invention without any limitations as to the variations that may be appreciated by the person skilled in the art. A non-limiting summary of various experimental results is given in the examples and tables, which demonstrate the advantageous and novel aspects of the process of using the azeotropic distillation technique for effective treatment of aqueous organic industrial effluents.

Having generally described the invention, a further understanding can be obtained by reference to certain specific examples which are provided herein for the purpose of illustration only, and are not intended to be limiting unless otherwise specified.

EXAMPLES

Compounds
Methyl isobutyl ketone
Isophorone,
Sulphuric acid, used for acid pre-treatment of lignocellulosic biomass,
NaOH, NaHCO$_3$, and MgO, used for pH adjustment, are available from Sigma-Aldrich.
Methods Analysis of methyl isobutyl ketone, isophorone, furfural and hydroxyl methyl furfural (HMF) in the aqueous effluent stream, distillate and treated effluent stream are done using standard gas chromatography (GC) procedures. For example, lab analytical procedures are available at National Renewable Energy lab (NREL) website http://www.nrel.gov/.

The Chemical oxygen demand (COD) is measured according to—American Public Health Association's Standard methods for the examination of water and was water. 22nd Edition 2012, page No 5-20 to 5-21 (section 5220 D. Closed Reflux Colorimetric Method) and;

The Biological oxygen demand (BOD) is measured according to—American Public Health Association's Standard methods for examination of water and waste water. 22nd Edition 2012, page No 5-5 to 5-10 (section 5210 B. 5-Day BOD Test).

Example 1

About 3.5 kg of a concentrated feedstock stream comprising 20 wt.-% xylose by weight was obtained from an acid pre-treated lignocellulosic biomass waste streams, for example, sugar cane bagasse. This stream also comprised about 2% sulphuric acid by weight used in said pre-treatment reaction. Then said stream was subjected to pH adjustment to a pH value of 1.6 using a 50% NaOH solution or powder of magnesium oxide. Then a mixture of 2800 g of methyl isobutyl ketone (MIBK) and 700 g of isophorone (in ratio of 80:20) was added to this stream forming a reaction mixture. This reaction mixture was subjected to a temperature of 180° C. in a closed stirred tank reactor working at 650 RPM for 1 hour. After completion of the heat treatment, the reaction mass so obtained was cooled to room temperature, and solids [solid humins] remaining in the mass were removed by filtration and allowed to separate in two phases: a main organic phase and an aqueous phase. Then said main organic phase was removed from aqueous phase [a. k. a. aqueous effluent stream in Example 2 & 3] and subjected to pH adjustment to 7 by NaHCO$_3$. The main organic phase was subjected to distillation to recover furfural, MIBK and isophorone. The aqueous effluent stream from multiple batches was obtained according to the procedure as discussed above. While said aqueous effluent stream was subjected to the process of the invention disclosed in examples below.

Example 2

The aqueous effluent stream obtained from example 1 comprised 4100 ppm (0.41% wt./wt.) of MIBK, 1600 ppm (0.16% wt./wt.) of isophorone, 2600 ppm (0.26% wt./wt.) of furfural and 1800 ppm (0.18% wt./wt.) of HMF (hydroxymethyl furfural) as organic components along with un-reacted sugars, soluble humins, soluble salts etc. The pH of the effluent was about 1.8 with a dark colouration. The chemical oxygen demand (COD) for this stream was high at 110000 ppm and biological oxygen demand (BOD) was 28000 ppm. To reduce the COD and to recover the organic components, said aqueous effluent stream of 11.5 kg (11500 g) was subjected to azeotropic distillation at 95° C. Said azeotropic distillation of aqueous effluent afforded 1.9 kg (1900 g) of distillate called a distillate stream [this was processed as per Example 5]. The distillate comprised a top organic layer of 50.70 g and a lower aqueous layer of 1851.3 g. The distillation bottom stream of said azeotropic distillation formed a treated effluent stream. The COD of said treated effluent stream decreased to 75,000 ppm. Thus, said azeotropic distillation step not only helped in recovery/recycle of organic solvents and furfural product but also reduced the COD by 32% of initial value in this step. This operation improved the overall economics of the furfural process and further improved the quality of said treated effluent stream to be subjected for biomethanation. The said treated effluent stream contained no MIBK, 100 ppm (0.01% wt./wt.) of isophorone, 500 ppm (0.05% wt./wt.) of furfural and 2100 ppm (0.21% wt./wt.) of HMF, as organic components [see Table 1]. The said azeotropic distillation step to recover the organic solvents removed more than 90% of the solvents that were able to form azeotropes with water. Next, said treated effluent stream was further subjected to pH adjustment to about 6 using magnesium oxide. This effluent was then subjected to a step of anaerobic biomethanation. The flow rate of said effluent stream to biomethanation reactor was between 10 to 30 L/day. The outlet stream pH was about 7.8. The final COD of the treated effluent stream was about 16,500 ppm after 45 days, showing about 78% step reduction in COD. Overall reduction in COD after azeotropic distillation and biomethanation was 85% of original COD value of the aqueous effluent stream. Similarly, the BOD values of the aqueous effluent stream were substantially reduced after azeotropic distillation step ie. by 20% of the original BOD value of the aqueous effluent stream and by a further biomethanation step ie. by 73% of the BOD value of the treated effluent stream. Thus, the overall reduction in BOD after azeotropic distillation and biomethanation was 79% of the original BOD value of the aqueous effluent stream [Table 1].

afforded 7.5 g of distillate called a distillate stream. The distillate comprised a top organic layer of 7.5 g and a lower aqueous layer of 110.2 g. The distillation bottom stream of said azeotropic distillation formed a treated effluent stream. The COD of said treated effluent stream decreased to 43,000 ppm. Thus, said azeotropic distillation step not only helped in recovery/recycle of organic solvents and furfural product but also reduced the COD by 40% of initial value in this step. This operation improved the overall economics of the furfural process and further improved the quality of said treated effluent stream to be subjected for biomethanation. The said treated effluent stream contained 100 ppm (0.01% wt./wt.) MIBK, 200 ppm (0.02% wt./wt.) of isophorone, 800 ppm (0.08% wt./wt.) of furfural and 1900 ppm (0.19% wt./wt) of HMF, as organic components [see Table 2]. The said azeotropic distillation step to recover the organic solvents removed more than 90% of the solvents that were able to form azeotropes with water. Next, said treated effluent stream was further subjected to pH adjustment to about 6 using magnesium oxide. This effluent was then subjected to a step of anaerobic biomethanation. The final COD of the

TABLE 1

Composition of streams after different steps

| | | After azeotropic distillation | | | |
| | Aqueous | Distillate | | | |
| Organic component | effluent Feed/stream | Top layer- organic | Lower layer- aqueous | Bottom (treated effluent stream | After biomethanation |
|---|---|---|---|---|---|
| Quantity (in g) | 11500 | 50.70 | 1851.3 | 9481.0 | |
| | % wt./wt. | % wt./wt. | % wt./wt. | ppm (% wt./ wt.) | ppm (% wt./ wt.) |
| MIBK (in % wt./wt.) | 0.41 | 62.33 | 0.87 | 0 | 0 |
| ISP (in % wt./wt.) | 0.16 | 18.40 | 0.31 | 100 (0.01) | 0 |
| Furfural (in % wt./wt.) | 0.26 | 13.46 | 1.13 | 500 (0.05) | 100 (0.01) |
| HMF (in % wt./wt.) | 0.18 | 00 | 00 | 2100 (0.21) | 1500 (0.15) |
| COD (in ppm) | 110000 | — | — | 75000 | 16500 |
| BOD (in ppm) | 28000 | | | 22500 | 6000 |

Example 3

The aqueous effluent stream obtained from example 1 comprised 6900 ppm (0.69% wt./wt.) of MIBK, 2700 ppm (0.27% wt./wt.) of isophorone, 3300 ppm (0.33% wt./wt.) of furfural and 1600 ppm (0.16% wt./wt.) of HMF as organic components along with un-reacted sugars, soluble humins, soluble salts etc. The pH of the effluent was about 1.8 with a dark colouration. The chemical oxygen demand (COD) for this stream was high at 72,000 ppm and biological oxygen demand (BOD) was 29000 ppm. To reduce the COD and to recover the organic components, said aqueous effluent stream of 700 g was subjected to azeotropic distillation at 95° C. Said azeotropic distillation of aqueous effluent treated effluent stream was about 22,000 ppm after 30 days, showing about 48% step reduction in COD. Overall reduction in COD after azeotropic distillation and biomethanation was 70% of original COD value of the aqueous effluent stream. Similarly, the BOD values of the aqueous effluent stream were substantially reduced after azeotropic distillation step ie. by 31% of the original BOD values of the aqueous effluent stream and by a further biomethanation step ie. by 35% of the BOD value of the treated effluent stream. Thus, the overall reduction in BOD after the azeotropic distillation and biomethanation was of 55% the original BOD value of the aqueous effluent stream.

TABLE 2

Composition of streams after different steps

| | | After azeotropic distillation | | | |
| | Aqueous | Distillate | | | |
| Organic component | effluent Feed/stream | Top layer- organic | Lower layer- aqueous | Bottom (treated effluent stream | After biomethanation |
|---|---|---|---|---|---|
| Quantity (in g) | 700 | 7.5 | 110.2 | 580 | |
| | % wt./wt. | % wt./wt. | % wt./wt. | ppm (% wt./ wt.) | ppm (% wt./ wt.) |
| MIBK (in % wt./wt.) | 0.69 | 58.49 | 1.13 | 100 (0.01) | 0 |

TABLE 2-continued

Composition of streams after different steps

| Organic component | Aqueous effluent Feed/stream | After azeotropic distillation | | Bottom (treated effluent stream) | After biomethanation |
|---|---|---|---|---|---|
| | | Distillate | | | |
| | | Top layer-organic | Lower layer-aqueous | | |
| ISP (in % wt./wt.) | 0.27 | 23.35 | 0.31 | 200 (0.02) | 0 |
| Furfural (in % wt./wt.) | 0.33 | 16.67 | 1.07 | 800 (0.08) | 200 (0.02) |
| HMF (in % wt./wt.) | 0.16 | 00 | 00 | 1900 (0.19) | 1300 (0.13) |
| COD, (in ppm) | 72000 | — | — | 43000 | 22000 |
| BOD, (in ppm) | 29000 | | | 20000 | 13000 |

Example 4

The separated solid humins of Example 1 also contained the solvents and the product. These organic compounds could not be easily recovered by washing with other solvents and other methods. Said solid humins were optionally added to the said aqueous effluent stream of Example 2 to recover said organic components from it. This way the solid humins after removal of said organic components were processed and stored safely for the future use in boilers for the energy generation.

Example 5

The said distillate stream of Example 2 comprised two phases wherein a top organic layer was 50.7 g and an aqueous layer was 1.85 kg (1851.3 g). The said top organic layer after isolation was mixed and processed with the main organic phase of Example 1. The said aqueous layer, containing finite amount of organic components, was recycled with said aqueous effluent stream of Example 1 increasing the general efficiency of the process of invention.

The invention claimed is:

1. A method of treatment of an aqueous effluent stream by subjecting the aqueous effluent stream containing at least one organic solvent, furfural and water to azeotropic distillation to obtain a distillate stream and a treated effluent stream, wherein the at least one organic solvent is selected from the group consisting of cyclic ketones, dialkyl ketones, and benzene derivatives.

2. The method according to claim 1, wherein the aqueous effluent stream is obtained by:
 i) pre-treating lignocellulosic biomass with mineral or organic acids to obtain a soluble C5 sugar fraction containing xylose;
 ii) adjusting a pH of the soluble C5 sugar fraction obtained in step i);
 iii) treating the pH adjusted soluble C5 sugar fraction with at least one organic solvent to obtain a feed stream with an aqueous phase and an organic phase;
 iv) subjecting the feed stream obtained in step iii) to a temperature in the range of ≥160° C. to ≤220° C. for a period in the range of ≥10 minutes to ≤2 hours, to obtain a reaction mass comprising furfural;
 v) filtering the reaction mass of step iv) to obtain a liquid fraction; and
 vi) subjecting the liquid fraction obtained in step v) to phase separation to obtain an organic phase comprising furfural and the at least one organic solvent, and the aqueous effluent stream comprising the at least one organic solvent, furfural and water.

3. The method according to claim 1, wherein the cyclic ketones are selected from the group consisting of isophorone, cyclohexanone and cyclopentanone.

4. The method according to claim 1, wherein the dialkyl ketones are selected from the group consisting of methyl isobutyl ketone, methyl ethyl ketone, dipropyl ketone, ethyl butyl ketone, diisobutyl ketone, methyl amyl ketone, methyl propyl ketone and 5-methyl-2-hexanone.

5. The method according to claim 1, wherein the benzene derivatives are selected from the group consisting of toluene, xylene, sec-butyl phenol, diphenyl oxide and methyl phenyl ketone.

6. The method according to claim 1, wherein the at least one organic solvent contains at least two organic solvents.

7. The method according to claim 6, wherein the at least two organic solvents are selected from the group consisting of isophorone, cyclohexanone, cyclopentanone, methyl isobutyl ketone, methyl ethyl ketone, dipropyl ketone, ethyl butyl ketone, diisobutyl ketone, methyl amyl ketone, methyl propyl ketone, 5-methyl-2-hexanone, toluene, xylene, sec-butyl phenol, diphenyl oxide and methyl phenyl ketone.

8. The method according to claim 6, wherein the at least two organic solvents are methyl isobutyl ketone and isophorone.

9. The method according to claim 1, wherein the azeotropic distillation is carried out at a temperature in the range of ≥80° C. to ≤100° C.

10. The method according to claim 1, wherein the azeotropic distillation is carried out at a pressure in the range of ≥650 mmHg to ≤760 mmHg.

11. The method according to claim 1, wherein a concentration of the at least one organic solvent in the aqueous effluent stream is in the range of ≥0.05 wt.-% to ≤2 wt.-%.

12. The method according to claim 4, wherein a concentration of methyl isobutyl ketone in the aqueous effluent stream is in the range of ≥0.15 wt.-% to ≤0.85 wt.-%.

13. The method according to claim 3, wherein a concentration of isophorone in the aqueous effluent stream is in the range of ≥0.05 wt.-% to ≤0.45 wt.-%.

14. The method according to claim 1, wherein a concentration of furfural in the aqueous effluent stream is in the range of ≥0.1 wt.-% to ≤0.5 wt.-%.

15. The method according to claim 1, further comprising the step of biomethanation of the treated effluent stream, subsequent to the azeotropic distillation.

16. A method for producing furfural using MIBK (methyl-isobutyl-ketone) and ISP (isophorone) as solvents for furfural, wherein MIBK, ISP and furfural are removed from an aqueous effluent in one distillation step.

* * * * *